(12) United States Patent
Pfeiffer et al.

(10) Patent No.: US 7,209,780 B2
(45) Date of Patent: Apr. 24, 2007

(54) SYSTEM AND A COMPUTER PROGRAM FOR THE DETERMINATION OF QUANTITIES RELATING TO THE CIRCULATORY SYSTEM OF A PATIENT

(75) Inventors: Ulrich J. Pfeiffer, Munich (DE); Thorsten Burger, Munich (DE)

(73) Assignee: Fulsion Medical Systems AG, Munich (DE)

( * ) Notice: Subject to any disclaimer, the term of this patent is extended or adjusted under 35 U.S.C. 154(b) by 571 days.

(21) Appl. No.: 10/222,973

(22) Filed: Aug. 19, 2002

(65) Prior Publication Data

US 2003/0060722 A1    Mar. 27, 2003

(30) Foreign Application Priority Data

Sep. 7, 2001    (DE) .................. 101 43 995

(51) Int. Cl.
*A61B 6/00*    (2006.01)
(52) U.S. Cl. .................. 600/431; 600/314; 600/317; 600/322; 600/323; 600/324; 600/484; 600/504; 600/526
(58) Field of Classification Search .............. 600/431, 600/317, 526, 481, 504, 505, 323, 473, 438
See application file for complete search history.

(56) References Cited

U.S. PATENT DOCUMENTS

| | | | |
|---|---|---|---|
| 3,618,591 A | | 11/1971 | Bradley et al. |
| 4,417,588 A | * | 11/1983 | Houghton et al. .......... 600/526 |
| 5,526,817 A | * | 6/1996 | Pfeiffer et al. ............. 600/504 |
| 5,687,726 A | * | 11/1997 | Hoeft ....................... 600/431 |
| 5,999,841 A | | 12/1999 | Aoyagi et al. |
| 6,071,244 A | | 6/2000 | Band et al. |
| 6,757,554 B2 | * | 6/2004 | Rubinstein et al. ......... 600/317 |

FOREIGN PATENT DOCUMENTS

| | | |
|---|---|---|
| DE | 41 30 931 A1 | 3/1993 |
| DE | 42 14 402 A1 | 11/1993 |
| EP | 0 059 032 A1 | 9/1982 |
| EP | 0 505 918 A1 | 9/1992 |
| WO | WO 00/01297 | 1/2000 |
| WO | WO 01/06920 A1 | 2/2001 |
| WO | 01/30237 A1 | 5/2001 |
| WO | WO 01/30237 A1 | 5/2001 |

OTHER PUBLICATIONS

European Search Report (dated Jun. 11, 2003).

* cited by examiner

*Primary Examiner*—Brian L. Casler
(74) *Attorney, Agent, or Firm*—Nixon Peabody LLP; Donald R. Studebaker

(57) ABSTRACT

A system for the determination of quantifies relating to the circulatory system of a patient including a device for the non-invasive measurement of the qualitative variation over time of the local concentration of an indicator injected into the blood circulation system at a first position, the measurement taking place at a second position of the blood circulation system. An evaluating unit is provided, in which there is implemented an evaluating algorithm which transforms the qualitative variation into a quantitative variation over time of the local concentration of the indicator injected into the blood circulation system. For the purposes of the transformation, the condition is fulfilled that the cardiac output COdye calculable from the quantitative variation over time of the local concentration in accordance with a predetermined relationship is equal to an input value of the cardiac output COe, which has been determined by thermodilution measurement.

49 Claims, 1 Drawing Sheet

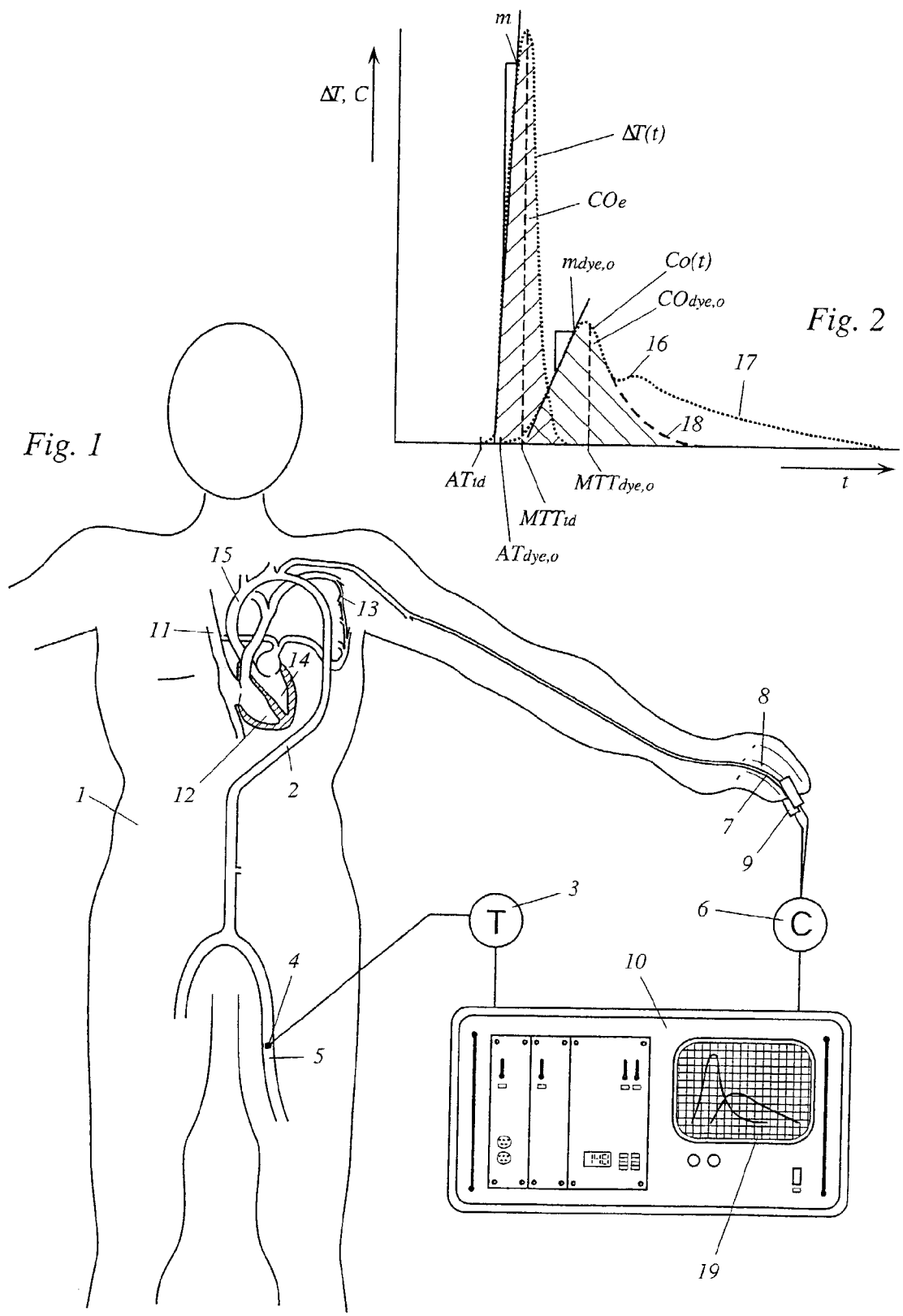

SYSTEM AND A COMPUTER PROGRAM FOR THE DETERMINATION OF QUANTITIES RELATING TO THE CIRCULATORY SYSTEM OF A PATIENT

BACKGROUND OF THE INVENTION

The present invention relates to a system and also to a computer program for the determination of quantities relating to the circulatory system of a patient, and especially for determining the circulating volume of blood and quantities derived therefrom by means of pulse spectrophotometric methods.

A system suitable for determining the circulating volume of blood is known, inter alia, from German patent document DE 41 30 931 Al. This is based on the principle of pulse spectrophotometry. Following the injection of a dye-bolus into the blood circulation system of a patient, the variation in the concentration of dye with respect to time is measured optically. This can be effected invasively by means of a fibre optic catheter or non-invasively by means of a reflection or transmission measurement at a finger, earlobe etc. A circulation transport function is then determined and a circulation response pulse that would correspond to an ideal indicator injection at a time point t=0 is calculated therefrom. A virtual dye concentration at the time point t=0 is then calculated by backward extrapolation of the circulation response pulse. The circulating volume of blood is given by the quotient of the amount of dye injected and the virtual dye concentration at the time point t=0. In the case of an invasive measurement, use is made of a fibre optic catheter which is technically relatively complex and expensive and, in addition, the application thereof imposes further stress on the patient. In the case of a non-invasive measurement, the problem of lack of precision in the measurement arises as will be discussed hereinbelow.

For the purposes of determining a plurality of quantities relating to the circulatory system, inter alia, the volume of blood that is circulating and the cardiac output CO by means of pulse spectrophotometric methods, it is necessary for the variation in the absolute concentration of the dye injected into the circulation to be known as precisely as possible, a qualitative measure for the variation of dye concentration over time is not sufficient. However, since the optical behaviour of biological tissue is mainly determined by the scattering of light so that the Lambert-Beer's law is no longer applicable, absolute concentrations cannot be determined by means of a non-invasive spectrophotometric measurement. A set-up for solving this problem is known from EP 0 505 918, wherein the ratio of the concentration of the injected dye to the concentration of a reference dye in the form of the haemoglobin that is always uniformly present in the blood and absorbs to a maximum extent in a differing wavelength range is determined. To this end, the extinction at the respective absorption maxima is determined by means of measurements at two different wavelengths. The absolute concentration of the haemoglobin in a blood sample is measured in vitro. A calibration is thereby effected, but this does not represent an online-calibration due to the in vitro measurement.

Other conventional non-invasive pulse spectrophotometric systems for the measurement of the circulating volume of blood, such as the system disclosed in U.S. Pat. No. 5,999,841, dispense with a calibration based on a blood sample and in vitro measurement of the haemoglobin concentration. However, the evaluating algorithms, which are based essentially on Lambert-Beer's law, cannot always ensure sufficient accuracy for the determined variations over time of the dye concentration and the quantities relating to the circulatory system derived therefrom due to the abovementioned scattering effects of biological tissue.

SUMMARY OF THE INVENTION

In the light of the problems outlined above in regard to conventional systems of the type described hereinabove, the object of the present invention is to provide a system which will permit a greater degree of precision and reliability in the determination of the quantities relating to the circulatory system that require a knowledge of the absolute indicator concentration when investigating by means of methods involving a measurement of the indicator concentration. In this context, it is to be understood that an indicator is a detectable material which will remain in the vascular system during a relevant period of measurement. In particular, the materials that can be used as indicators are those which absorb electromagnetic radiation in the visible or invisible spectral range. Here, it is dyes which primarily come into consideration. The object of the invention lies particularly in the provision of a system with whose help the circulating volume of blood and the quantities derived therefrom can be determined with a greater degree of precision and reliability than is the case with conventional systems based upon the principle of pulse spectrophotometry.

In accordance with a first aspect of the invention, there is provided a system for the determination of quantities relating to the circulatory system of a patient, comprising a device for the non-invasive measurement of the qualitative variation over time of the local concentration of an indicator injected into the blood circulation system at a first position, said measurement taking place at a second position of the blood circulation system and an evaluating unit which comprises an input interface for reading in an input value of the cardiac output $CO_e$ of the patient, and in which there is implemented an evaluating algorithm which transforms the qualitative variation over time of the local concentration of the indicator injected into the blood circulation system into a quantitative variation over time of the local concentration of the indicator injected into the blood circulation system, wherein the condition is fulfilled that the cardiac output $CO_{dye}$, which is calculable from the quantitative variation over time of the local concentration according to a predetermined relationship, is equal to the input value of the cardiac output $CO_e$.

Thus, the system envisages, so to say, a calibration of the indicator concentration measurement by means of an otherwise determined input value of the cardiac output $CO_e$ which preferably originates from a (preferably transpulmonary) thermodilution measurement. From the quantitative indicator concentration curve obtained thereby, the starting concentration of the injected indicator with reference to the circulating volume of blood TBV can be determined by backward extrapolation of the exponentially falling branch of the curve to the ordinate. The circulating volume of blood TBV can then be calculated by forming the quotient of the injected quantity of indicator and the starting concentration that has been determined with reference to the circulating volume of blood TBV.

Thus, in contrast to the systems described above which were based upon a dye concentration measurement wherein the in vitro determination of the haemoglobin concentration as a reference dye is necessary in order to obtain absolute concentration values, the invention preferably envisages a calibration by means of values that are determined contemporaneously and online.

If provision is made for a transpulmonary thermodilution measurement, which has the advantage that a Swan-Ganz catheter—which is problematical because of the high risks involved when using it—does not need to be used, then, for example, the upper vena cava is a suitable first position for the injection of the cooled bolus containing the indicator, and the femoral artery or the axillary artery is suitable for the measurement of the variation over time of the local blood temperature.

In addition, by virtue of the combination of the indicator concentration measurement and a transpulmonary thermodilution measurement, quantities relating to the circulatory system can be determined which are not accessible by a measurement that is based purely on the indicator concentration for reasons of principle, in particular, the intrathoracic thermovolume ITTV and the extravascular thermovolume ETV which is calculable therefrom and is closely correlated to the extravascular pulmonary fluid insofar as there is no significant perfusion defect in the lungs, such as perhaps a pulmonary embolism.

A wavelength of 805 nm is particularly advantageous for the determination of the qualitative variation over time of the local concentration of the dye indocyanin-green that is preferably employed as the indicator because the maximum absorption of indocyanin-green occurs at 805 nm.

In accordance with a second aspect of the invention, there is provided a computer program for determining quantities relating to the circulation system of a patient, comprising an evaluating algorithm which is executable by a computer and which processes input data in the form of the qualitative variation over time of the local concentration of an indicator injected into the blood circulation system at a first position wherein said variation is determined by a non-invasive measurement at a second position of the blood circulation system, said evaluating algorithm transforming the qualitative variation over time of the local concentration of the indicator injected into the blood circulation system into a quantitative variation over time of the local concentration of the indicator injected into the blood circulation system, wherein the condition is fulfilled that the cardiac output Codye, which is calculable from the quantitative variation over time of the local concentration in accordance with a predetermined relationship, is equal to an input value of the cardiac output COe which is determined in some other manner.

In accordance with a third aspect of the present invention, there is provided a storage medium upon which is physically stored a computer program in accordance with the second aspect.

BRIEF DESCRIPTION OF THE DRAWINGS

A preferred embodiment of the invention will now be described, by way of example only, with reference to the accompanying drawings, of which:

FIG. 1 shows, in purely schematic manner, the construction of a system in accordance with the invention and also a section of the blood circulation system of a patient for whom quantities relating to the circulatory system are to be determined by utilisation of the system; and FIG. 2 shows, likewise in purely schematic manner, the variation over time of the deviation of the local blood temperature $\Delta T(t)$ with respect to the normal temperature that was determined by the system in accordance with the invention following the injection into the blood circulation system of a bolus containing an indicator cooled below body temperature and also the corresponding qualitative variation over time of the local concentration of the indicator injected into the blood circulation system prior to the transformation into a corrected quantitative variation over time of the local concentration $Co(t)$ of the indicator injected into the blood circulation system. The abscissa functions as a time axis, the ordinate as a temperature or concentration axis.

DESCRIPTION OF THE PREFERRED EMBODIMENTS

FIG. 1 shows the schematic construction of a system in accordance with the invention. The system will be described in terms of its application for the determination of quantities relating to the circulatory system of a patient 1 whose blood circulation system 2 is partially illustrated likewise in schematic manner. The system comprises a temperature sensor 3 whose envisaged position of measurement 4 is accessible in the femoral artery 5 of the patient 1 by employment of an arterial catheter (not illustrated).

Furthermore, the system is equipped with a spectrometric concentration measuring unit 6 for the measurement of the local concentration of indocyanin-green (ICG) in the blood vessels 7 of a finger 8 of the patient 1. To this end, the concentration measuring unit 6 comprises two light emitters (not illustrated) for emitting electromagnetic waves in the near infrared range as well as two appertaining NIR-sensors which are integrated into a finger clip 9. The respective light emitters are designed for the production of electromagnetic radiation having a wavelength of 805 nm, which corresponds to the absorption maximum of ICG, and radiation of approximately 900 nm. The near infrared radiation is guided by means of light guides, i.e. fibre optic bundles (not illustrated), to exit points on the finger clip 9 where it is emitted. As an alternative, light emitting diodes that emit the desired wavelengths could also be placed directly on the finger clip 9. The NIR sensors located opposite the exit points capture the respective non-absorbed components of the emitted radiation that is transmitted through the finger. An arrangement comprising just one NIR sensor, which is sufficiently sensitive at 805 nm and also at 900 nm, is also conceivable. In this case, the respective NIR light pulses of 805 nm and 900 nm are transmitted shortly after one another, i.e. mutually time delayed, so that the radiation received by the sensor can be associated with the one or the other wavelength based upon the relevant time point.

The smaller the intensity of the transmitted radiation of wavelength of 805 nm in proportion to the intensity of the transmitted radiation of wavelength 900 nm, so the greater the concentration of indocyanin-green that is contained in the blood. The conversion of the measured intensities into relative concentration values is effected by the methods known from the field of pulse oxymetry.

Both the temperature sensor 3 and the spectrometric concentration measuring unit 6 are connected to the control and evaluating unit integrated in a computer 10. The computer program in accordance with the invention is installed on the computer 10, this program incorporating the evaluating algorithm whose functioning will be described below.

The functioning of the system in accordance with the invention and of the program in accordance with the invention that is installed on the computer 10 will become particularly clear from the course of a typical measurement which will be described hereinafter.

A defined quantity of indocyanin-green that is cooled to below body temperature is injected as a bolus into the upper vena cava 11 of the patient 1. The indicator molecules and the local temperature deviation are transported by the blood circulation system through the right-hand ventricle 12, the pulmonary system 13 and the left-hand ventricle 14 of the patient 1 and thus arrive in the aorta 15. The local temperature curve $\Delta T(t)$ and the qualitative indicator concentration curve Co(t), which are measured further downcirculation system at the measuring positions in the femoral artery 5 and the vessels 7 of the finger 9, are registered as the system response of the circulation system to the bolus injection and serve as input data for the evaluating algorithm in the computer program installed on the computer 10.

A typical temperature curve $\Delta T(t)$—which is also referred to as a thermodilution curve—and a qualitative indicator concentration curve Co(t) are illustrated in FIG. 2. The local variation over time of the temperature difference $\Delta T$ is plotted positively, whereby it should be noted that, de facto, there will be local cooling over time. Due to the longer transportation time up to the position at which the concentration is measured, which is recognizable by the uncorrected time of appearance of the alteration in concentration $ATdye,o$ which is later relative to the time of appearance of the alteration in temperature ATtd, the qualitative indicator concentration curve Co(t) will turn out to be flatter and broader than the temperature curve $\Delta T(t)$ because of the diffusive spread of the indicator molecules. This is recognizable by virtue of the respectively plotted slope-triangles m and mdye,o of the straight line approximations, which have been constructed along the respective rising flanks of the curves. The respective slopes m and mdye,o correspond hereby to the average slope of the rising flank in a range from 20% to 80% of the maximum of the respective curve. In addition, a second rise in concentration 16 due to the recirculation of the indicator molecules is apparent, whereafter there is an exponential fall 17 of the indicator concentration which stems from the degradation of the indocyanin-green in the liver. It is assumed that the concentration of the indicator in the vascular system is uniform over the range of the exponential fall 17.

Furthermore, the average transit time of the temperature alteration MTTtd and also the uncorrected average transit time of the indicator MTTdye,o have been plotted. For the reason as to why the temperature curve $\Delta T(t)$ comes about, one must take into consideration that a heat exchanging process, for example with extravascular pulmonary fluid, takes place along the transport path through the pulmonary system 13, this thereby resulting in a displacement of the average transit time of the temperature alteration MTTtd.

The evaluating algorithm transforms the qualitative indicator concentration curve Co(t) into a corrected quantitative indicator concentration curve (not illustrated). The transformation is effected in such a manner that the following three conditions are fulfilled:

1) The cardiac output COdye resulting from the corrected quantitative variation over time of the local concentration is equal to the cardiac output COe resulting from the variation over time of the local temperature alteration $\Delta T(t)$. Hereby, one resorts to the known Stewart-Hamilton relationship for the cardiac output CO, this being represented by the highlighting of the area under the thermodilution curve.

It should be noted that recirculated indicator should not be taken into consideration for the determination of COdye. This can be effected perhaps, by extrapolating the first falling branch of the curve representing the variation in the concentration of the indicator over time to the abscissa. Such an extrapolation 18 of the qualitative indicator concentration time curve is shown for the sake of illustration.

However for the purpose of determining COdye, it is more expedient to make use only of the rising branch of the curve of the variation in the concentration of indicator over time up to the maximum, and to take advantage of a relationship that is known for intravascular measured dilution curves: according thereto, the area under a typical intravascular dilution curve that is measured e.g. in the femoral artery or the axillary artery corresponds approximately to 2.5- to 3-times, in general 2.58-times, the area under the rising branch of the curve representing the variation in the concentration of indicator over time up to the maximum. This has been confirmed from the evaluation of a plurality of measured intravascular dilution curves. Thus, it is expedient if one determines COdye as a value which is proportional to the reciprocal of the integral of the time variance of the indicator concentration over the time interval up to the maximum. In order to simplify the computing effort, the rising branch of the curve could also be linearly approximated for this purpose.

2) A defined range, for example from 20% to 80% of the maximum, of the rising flank of the quantitatively corrected variation over time of the local concentration and also the variation over time of the local blood temperature $\Delta T(t)$ has the same average slope m.

Alternatively, the condition could be reformulated to say that a defined range, for example from 20% to 80% of the maximum, of the rising branch of the curve extends over a time which has a predetermined relationship to a comparison value obtained from an intravascular measurement. Here too, one may resort to a linear approximation of the rising branch of the curve. In end effect, the fulfilment of this condition amounts to a transformation of the abscissa, which is linear to a good approximation.

3) The time of appearance ATdye of the quantitatively corrected variation over time of the local indicator concentration is equal to the time of appearance ATtd of the variation over time of the local blood temperature $\Delta T(t)$.

From the so obtained corrected quantitative indicator concentration curve, the evaluating algorithm determines the starting concentration of the injected indicator with reference to the circulating volume of blood TBV by a process of backward extrapolation of the exponentially falling branch of the curve to the ordinate at the time point of the injection or, as a near approximation, to the time point of appearance ATdye. The circulating volume of blood TBV is calculated by forming the quotient of the injected quantity of indicator and the starting concentration determined with reference to the circulating volume of blood TBV.

Furthermore, the evaluating algorithm comprises the calculation of the following quantities relating to the circulatory system: the intrathoracic volume of blood ITBV as the product of the cardiac output CO and the average transit time MTTdye obtained from the corrected quantitative variation over time of the local concentration of the indicator injected into the blood circulation system, furthermore, the intrathoracic thermovolume ITTV as the product of the cardiac output COe and the average transit time MTTtd obtained from the variation over time of the local blood temperature.

The evaluating algorithm calculates the extravascular thermovolume ETV, which correlates to the extravascular pulmonary fluid EVLW, by forming the difference between the intrathoracic volume of blood ITBV and the intrathoracic thermovolume ITTV.

The peripheral perfusion is calculated by forming the difference between the average transit time MTTdye obtained from the corrected quantitative variation over time of the local concentration of the indicator injected into the blood circulation system and the average transit time MTTdye,o obtained from the qualitative variation over time of the local concentration of the indicator injected into the blood circulation system.

Furthermore, the evaluating algorithm calculates the rate of degradation of the indicator, the PDR, from the exponential fall over time of the quantitative or of the qualitative variation over time of the local concentration of the indicator injected into the blood circulation system after it is assumed that complete mixing thereof has taken place.

The determined quantities relating to the circulatory system are indicated on a monitor 19 and are additionally stored on a data recording medium, a diskette or a memory chip perhaps. Via a suitable interface, the determined quantities relating to the circulatory system could also be provided for cataloguing or documentation purposes by means of a printer.

It will be understood that the above description of the present invention is susceptible to various modification, changes and adaptations.

What is claimed is:

1. A system for the determination of quantities relating to the circulatory system of a patient, comprising a device for the non-invasive measurement of the qualitative variation over time of the local concentration of an indicator injected into the blood circulation system at a first position, said measurement taking place at a second position of the blood circulation system and an evaluating unit which comprises an input interface for reading in an input value of the cardiac output COe of the patient, said input interface being connected to a device for measurement of the variation over time of the local blood temperature at a third position of the blood circulation system of the patient after the injection into the blood circulation system at the first position of a bolus which contains the indicator and has a temperature below body temperature, and said device being equipped to determine and provide said input value of the cardiac output COe from the variation over time of the local blood temperature in accordance with methods commonly used fir thermodilution measurements, wherein an evaluating algorithm is implemented in said evaluating unit which transforms the qualitative variation over time of the local concentration of the indicator injected into the blood circulation system into a quantitative variation over time of the local concentration of the indicator injected into the blood circulation system, wherein the condition is fulfilled that the cardiac output COdyc, which is calculable from the quantitative variation over time of the local concentration according to a predetermined relationship, is equal to the input value of the cardiac output COe.

2. A system in accordance with claim 1, wherein the cardiac output COdyc according to the predetermined relationship is proportional to the reciprocal of the integral of the quantitative time variance of the local concentration over the time interval up to the maximum of the quantitative time variance of the local concentration.

3. A system in accordance with claim 2, wherein the evaluating algorithm implemented in the evaluating unit transforms the qualitative variation over time of the local concentration of the indicator injected into the blood circulation system into a corrected quantitative variation over time of the local concentration of the indicator injected into the blood circulation system, in that the time axis is transformed in such a manner that a defined range of the rising flank of the quantitatively corrected time variance of the local concentration extends over a time interval which has a predetermined relationship to a comparison value.

4. A system in accordance with claim 3, wherein the time axis is transformed by means of a transport function g(t).

5. A system in accordance with claim 4, wherein the transport function g(t) is approximated with the help of the equation $$Co*(t) = \int_{ATtd}^{T\max} g(t-u)\Delta T(u)du$$

wherein Co*(t) is the rising flank of the qualitative indicator concentration curve, ATtd is the time point of appearance of the cooled bolus, .DELTA.T(t) is the variation over time of the local blood temperature alteration, Tmax is the time point at which the local blood temperature alteration reaches its maximum value and u is an integration variable.

6. A system in accordance with claim 2, wherein the evaluating algorithm implemented in the evaluating unit transforms the qualitative variation over time of the local concentration of the indicator injected into the blood circulation system into a corrected quantitative variation over time of the local concentration of the indicator injected into the blood circulation system, in that the time axis is transformed in such a manner that a defined range of the rising flank of the quantitatively corrected variation over time of the local concentration has an average slope m which has a predetermined relationship to a comparison value.

7. A system in accordance wit claim 6, wherein the time axis is linearly transformed.

8. A system in accordance with claim 6, wherein the comparison value corresponds to the avenge slope, over which extends a defined range of the rising flank of the time variance of the local blood temperature corresponding to the defined range of the rising flank of the quantitatively corrected time variance.

9. A system in accordance with claim 8, wherein, in the course of the transformation, the condition is additionally fulfilled, that the quantitatively corrected variation over time of the local concentration has the same time of appearance .DELTA.T as the variation over time of the local blood temperature.

10. A system in accordance with claim 9, wherein the evaluating algorithm calculates the peripheral perfusion by forming the difference between the average transit time MTTdye obtained from the corrected quantitative variation over time of the local concentration of the indicator injected into the blood circulation system and the average transit time MTTdye,o obtained from the qualitative variation over time of the local concentration of the indicator injected into the blood circulation system.

11. A system in accordance with claim 9, wherein the evaluating algorithm calculates the peripheral perfusion by forming the difference between the time of appearance ATdye obtained from the corrected quantitative variation over time of the local concentration of the indicator injected into the blood circulation system and the time of appearance ATdye,o obtained from the qualitative variation over time of the local concentration of the indicator injected into the blood circulation system.

12. A system in accordance wit claim 3, wherein the time axis is linearly transformed.

13. A system in accordance with claim 3, wherein the comparison value corresponds to the time period over which extends a defined range of the rising flank of the time variance of the local blood temperature corresponding to the defined range of the rising flank of the quantitatively corrected time variance.

14. A system in accordance with claim 3, wherein the defined range extends from 20% to 80% of the maximum of the quantitatively corrected variation over time of the local concentration.

15. A system in accordance with claim 1, wherein the cardiac output COdye according to the predetermined relationship is proportional to the reciprocal of the integral of a linear approximation of the rising flank of the quantitative time variance of the local concentration over the time interval up to the maximum of the quantitative time variance of the local concentration.

16. A system in accordance with claim 1, wherein the evaluating algorithm determines the starting concentration of the injected indicator with reference to the circulating volume of blood TBV from the quantitative variation over time of the local concentration of the indicator injected into the blood circulation system and calculates the circulating volume of blood TBV by forming the quotient of the injected quantity of indicator and the starting concentration determined with reference to the circulating volume of blood TBV.

17. A system in accordance with claim 16, wherein the starting concentration of the injected indicator is determined by backward extrapolation of the variation over time of the local concentration of the indicator injected into the blood circulation system up to the time point of appearance ATdye of the indicator or up to the time point of the injection of the indicator.

18. A system in accordance with claim 16, wherein the evaluating algorithm also calculates the intrathoracic volume of blood ITBV as the product of the cardiac output COe and the average transit time MTTdye obtained from the corrected quantitative variation over time of the local concentration of the indicator injected into the blood circulation system.

19. A system in accordance with claim 1, wherein the evaluating algorithm also calculates the intrathoracic thermovolume ITTV as the product of the cardiac output COe and the average transit time MTTtd obtained from the variation over time of the local blood temperature.

20. A system in accordance with claim 19, wherein the evaluating algorithm calculates the extravascular thermovolume ETV by forming the difference between the intrathoracic volume of blood ITBV and the intrathoracic thermovolume ITTV.

21. A system in accordance with claim 1, wherein the evaluating algorithm also calculates the rate of degradation of the indicator PDR from the exponential fall over time of the quantitative time variance of the local concentration of the indicator injected into the blood circulation system after it is assumed that the mixing process is complete.

22. A system in accordance with claim 1, wherein the evaluating algorithm also determines the proportion of the indicator remaining in the blood after a predefined time span.

23. A system in accordance with claim 1, wherein the indicator is indocyanin-green and the device for the non-invasive measurement of the qualitative variation over time of the local concentration comprises means for the transmission of near infrared electromagnetic waves and a sensor which is sensitive in the near infrared range.

24. A system in accordance with claim 23, wherein the non-invasive measurement of the qualitative variation over time of the local concentration is a transmission measurement that is to be effected on a finger, a toe, the nose or an ear of the patient.

25. A system in accordance with claim 23, wherein the means for the transmission of near infrared electromagnetic waves are equipped for the production of at least two different wavelengths, and the system is equipped in such a manner that the intensities of the different wavelengths can be selectively detected by means of the sensor.

26. A system in accordance with claim 25, wherein one of the different wavelengths amounts to approximately 805 nm.

27. A system in accordance with claim 1, wherein means for determining the input value of the cardiac output COe from the variation over time of the local blood temperature employing the methods that are commonly used for a thermodilution measurement process are integrated in the evaluating unit, and wherein the input interface for reading in the input value of the cardiac output COe is a virtual or physically implemented internal interface of the evaluating unit.

28. A system in accordance with claim 1, wherein the system also comprises means for the measurement of the variation over time of the central venous blood pressure and also the variation over time of the arterial blood pressure, and wherein a further evaluating algorithm for carrying out a pulse contour analysis using the measured variation over time of the central venous blood pressure and the arterial blood pressure is implemented in the evaluating unit.

29. A storage medium having stored thereon a computer program for determining quantities relating to the circulation system of a patient, comprising an evaluating algorithm which is executable by a computer and which processes input data in the form of the qualitative variation over time of the local concentration of an indicator injected into the blood circulation system at a first position, wherein said variation is determined by a non-invasive measurement at a second position of the blood circulation system, said evaluating algorithm processing as further input data the variation over time of the local blood temperature measured at a third position of the blood circulation system of the patient after the injection of a bolus into the blood circulation system at the first position where said bolus has a temperature below body temperature and contains the indicator, said evaluating algorithm transforming the qualitative variation over time of the local concentration of the indicator injected into the blood circulation system into a quantitative variation over time of the local concentration of the indicator injected into the blood circulation system, wherein the condition is fulfilled that the cardiac output Codye, which is calculable from the quantitative variation over time of the local concentration in accordance with a predetermined relationship, is equal to an input value of the cardiac output COe which is determined from said further input data by methods commonly used for thermodilution measurements.

30. A storage medium in accordance with claim 29, wherein the cardiac output COdye in accordance with the predetermined relationship is proportional to the reciprocal of the integral of the quantitative time variance of the local concentration over the time interval up to the maximum of the quantitative time variance of the local concentration.

31. A storage medium in accordance with claim 29, wherein the cardiac output COdyc in accordance with the predetermined relationship is proportional to the reciprocal of the integral of a linear approximation of the rising flank of the quantitative time variance of the local concentration over the time interval up to the maximum of the quantitative time variance of the local concentration.

32. A storage medium in accordance with claim 29, wherein the evaluating algorithm transforms the qualitative variation over time of the local concentration of the indicator injected into the blood circulation system into a corrected quantitative variation over time of the local concentration of the indicator injected into the blood circulation system, the time axis being transformed in such a manner that a defined range of the rising flank of the quantitatively corrected time variance of the local concentration extends over a time interval which has a predetermined relationship to a comparison value.

33. A storage medium in accordance with claim 32, wherein the time axis is transformed by means of a transport function g(t).

34. A storage medium in accordance with claim 32, wherein the time axis is linearly transformed.

35. A storage medium in accordance with claim 32, wherein the comparison value corresponds to the period of time over which extends a defined range of the rising flank of the time variance of the local blood temperature corresponding to the defined range of the rising flank of the quantitatively corrected time variance.

36. A storage medium in accordance with claim 32, wherein the defined range extends from 20% to 80% of the maximum of the quantitatively corrected variation over time of the local concentration.

37. A storage medium in accordance with claim 29, wherein the transport function g(t) is approximated with the help of the equation $$Co*(t) = \int_{ATtd}^{T\,max} g(t-u)\Delta T(u)du$$

wherein Co*(t) is the rising flank of the qualitative indicator concentration curve, ATtd is the time of appearance of the cooled bolus, .DELTA.T(t) is the variation over time of the local blood temperature alteration, Tmax is the time point at which the local blood temperature alteration reaches its maximum value, and u is an integration variable.

38. A storage medium in accordance with claim 29, wherein the evaluating algorithm transforms the qualitative variation over time of the local concentration of the indicator injected into the blood circulation system into a corrected quantitative variation over time of the local concentration of the indicator injected into the blood circulation system, in that
the time axis is transformed in such a manner that a defined range of the rising flank of the quantitatively corrected time variance of the local concentration has an avenge slope which has a predetermined relationship to a comparison value.

39. A storage medium in accordance with claim 38, wherein the time axis is linearly transformed.

40. A storage medium in accordance with claim 38, wherein the comparison value corresponds to the average slope over which extends a defined range of the rising flank of the time variance of the local blood temperature corresponding to the defined range of the rising flank of the quantitatively corrected time variance.

41. A storage medium in accordance with claim 38, wherein, in the course of the transformation, the condition is additionally fulfilled that the quantitatively corrected variation over time of the local concentration has the same time of appearance AT as the variation over time of the local blood temperature.

42. A storage medium in accordance with claim 29, wherein the evaluating algorithm determines the starting concentration of the injected indicator taken with reference to the circulating volume of blood TBV from the quantitative variation over time of the local concentration of the indicator injected into the blood circulation system, and calculates the circulating volume of blood TBV by forming the quotient of the injected quantity of indicator and the determined starting concentration taken with reference to the circulating volume of blood TBV.

43. A storage medium in accordance with claim 42, wherein the starting concentration of the injected indicator is determined by backward extrapolation of the variation over time of the local concentration of the indicator injected into the blood circulation system up to the time point of appearance ATdye of the indicator or up to the time point of the injection of the indicator.

44. A storage medium in accordance with claim 42, wherein the evaluating algorithm also calculates the intrathoracic volume of blood ITBV as the product of the cardiac output COe and the average transit time MTTdye obtained from the corrected quantitative variation over time of the local concentration of the indicator injected into the blood circulation system.

45. A storage medium in accordance with claim 29, wherein the evaluating algorithm also calculates the intrathoracic thermovolume ITTV as the product of the cardiac output COe and the average transit time MTTtd obtained from the variation over time of the local blood temperature.

46. A storage medium in accordance with claim 45, wherein the evaluating algorithm calculates the extravascular thermovolume ETV by forming the difference between the intrathoracic volume of blood ITBV and the intrathoracic thermovolume ITTV.

47. A storage medium in accordance with claim 29, wherein the evaluating algorithm calculates the peripheral perfusion by forming the difference between the average transit time MTTdye obtained from the corrected quantitative variation over time of the local concentration of the indicator injected into the blood circulation system and the average transit time MTTdye,o obtained from the qualitative variation over time of the local concentration of the indicator injected into the blood circulation system.

48. A storage medium in accordance with claim 29, wherein the evaluating algorithm calculates the peripheral perfusion by forming the difference between the time of appearance ATdye obtained from the corrected quantitative variation over time of the local concentration of the indicator injected into the blood circulation system and the time of appearance ATdye,o obtained from the qualitative variation over time of the local concentration of the indicator injected into the blood circulation system.

49. A storage medium in accordance with claim 29, wherein the evaluating algorithm also calculates the rate of degradation of the indicator PDR from the exponential fall over time of the quantitative or qualitative time variance of the local concentration of the indicator injected into the blood circulation system after it is assumed that mixing is complete.

* * * * *